United States Patent [19]
Naylor et al.

[11] Patent Number: 5,980,958
[45] Date of Patent: Nov. 9, 1999

[54] FUNGAL FOOD

[75] Inventors: Thomas William Naylor, Stockton; Trevor Williamson, Seaham; Anthony Peter Joseph Trinci, Stockport; Geoffrey David Robson, Whalley Range; Marilyn Gail Wiebe, Stockport, all of United Kingdom

[73] Assignee: Zeneca Limited, London, United Kingdom

[21] Appl. No.: 09/091,105

[22] PCT Filed: Dec. 9, 1996

[86] PCT No.: PCT/GB96/03046

§ 371 Date: Jun. 12, 1998

§ 102(e) Date: Jun. 12, 1998

[87] PCT Pub. No.: WO97/22686

PCT Pub. Date: Jun. 26, 1997

[30] Foreign Application Priority Data

Dec. 16, 1995 [GB] United Kingdom .................. 9525902

[51] Int. Cl.$^6$ .................................. C12N 1/14; A23J 1/18
[52] U.S. Cl. ........................ 426/61; 426/656; 435/256.5
[58] Field of Search ........................ 435/256.5; 426/61, 426/656

[56] References Cited

U.S. PATENT DOCUMENTS

| | | | |
|---|---|---|---|
| 4,041,189 | 8/1977 | Towersey et al. | 426/656 |
| 4,163,692 | 8/1979 | Yates | 435/254 |

FOREIGN PATENT DOCUMENTS 24 45 254  4/1975  Germany .

OTHER PUBLICATIONS

Biotechnology Letters, vol. 8, No. 5, 1986, pp. 323–326, XP000197054 J.D.Bu'lok et al: "Regulation of mycotoxin production by *Fusarium graminearum*: complementation effects between two mutant types".

Mycological Research, vol. 95, No. 11, 1991, pp. 1284–1288, XP000197035, M.B.Wiebe et al: "Appearance of morphological (colonial) mutants in glucose–limited, continuous flow cultures of *Fusarium graminearum*A3/5".

Microbiology, vol. 140, No. 11, 1994, pp. 3015–3021, IP000197157, M.G. Wiebe et al: "Use of a series of chemostat cultures to isolate 'improved' variants of the Quorn (R) mycoprotein fungus, Fusarium graminearum A3/5".

J.S.Smith et al: The filamentous fungi, vol. 1, 1975, Industrial Mycology, XP000197032.

Food Laboratory Newsletter, vol. 6, No. 6, 1986, pp. 21–24, XP000197156, G. Edwards: "Myco–protein–the development of a new food".

Nature, vol. 287, No. 5777, 1980, p. 6, XP000647700, P. Newmark: "Meat substitutes. Fungal food".

Microbiology, vol. 142, No. 3, 1996, pp. 525–532, XP000197270, M.G.Wiebe et al: "How do highly branched (colonial) mutants of *Fusarium graminearum* A3/5 arise during Quorn ( R ) mycoprotein fermentations?".

*Primary Examiner*—Keith D. Hendricks
*Attorney, Agent, or Firm*—Pillsbury Madison & Sutro LLP

[57] ABSTRACT

A human food product comprises a higher ploidy strain of *Fungi imperfecti* of which each parent has a genetic growth constraint not shared by the other parent. One parent is for example auxotrophic for two compounds selected from histidine, arginine, leucine and adenine and the other for the other two. The nucleic acid content of the strain is preferably less than 2% by weight. The strain may be made by killing a higher ploidy strain of *Fungi imperfecti* and simultaneously reducing its nucleic acid content to below 2% by weight by treatment with water. The process may include preparing a higher ploidy strain of edible Fusarium by culturing two auxotrophs thereof together in a medium containing nutrients permitting both to grow and then culturing organisms derived from such culture in minimal medium. The invention is applicable to the production of human food by culturing the strain in conditions such that reversion or partial reversion to the haploid form(s) is minimised.

20 Claims, No Drawings

FUNGAL FOOD

This Invention relates to fungus.

Human foodstuffs are produced commercially from Fusarium which is a haploid fungus. A particularly suitable strain of Fusarium A3/5, IMI 145425 is described in U.S. Plant Pat. No. 4,347.

It is desirable in order to produce human foodstuffs of attractive mouth feel that the Fusarium should show little hyphal branching, and this is the case with Fusarium, IMI 145425. However, Fusarium in extended continuous fermentation invariably becomes more highly branched due to the appearance of variants in the fermenter culture. The appearance of highly branched variants appears to be a common feature of extended fungal fermentations. (Trinci, A. P. J, et al., (1990) Microbial Growth Dynamics, pp 17–38, IRL Press, Oxford U.K.)

It is therefore desirable that strains of Fusarium, of greater morphological stability should be produced.

In fungal strain breeding programmes the parasexual cycle has often been reported as a valuable means of improving commercially important production strains, since it enables the advantageous characteristics of two individuals to be combined via recombination, heterokaryosis or diploidy. For example, diploids have been claimed to give increased productivity of citric acid (Das & Roy, 1978), penicillin (Elander et al., 1973), and cephalosporin C (Takeda Chemical co., 1977). Reports of qualitative improvements include restoration of sporulation ability in *P. chrysogenum* (Calam et al., 1976), improved filtration characteristics in A, niger (Ball et al., 1978), generally improved vigour in *C. acremonium* (Hamlyn & Ball, 1979), reduced oxygen demand in *M. inyoensis* (Crueger, 1982), and elimination of p-hydroxypenicillin V production in *P. chrysogenum* (Chang et al., 1982). By contrast there appears to be no clear demonstration of parasexuality in Fusarium (Booth, 1984) although putative diploids of *F. oxysporum* have been described (Buxton, 1956). Attemps to demonstrate the production of diploids of *F. graminearum* NRRL 319 (Bu'Lock et al., 1986) were unsuccessful but heterokaryotes were reported.

According to Rowlands (1984) diploids are unstable and are likely to break down during fermentation with progressive loss of productivity unless some sort of selection pressure can be applied. In *S. cerevisiae* there is evidence that adaptive mutations occur at a higher (×1.6) frequency in an evolving diploid than in haploid populations (Paquin and Adams, 1983). This supports the view that diploid populations of fungi are unstable. We have however found that certain higher ploidy strains of fungi imperfecti show an increase in (morphological) stability under typical growth conditions relative to the parental haploids.

We have now made strains of Fusarium of higher ploidy and have devised means whereby other higher ploidy strains of *Fungi imperfecti* especially Fusarium may be produced. These have better morphological stability than haploid strains. It is thought possible that this may be at least partly due to reduced sensitivity to mutation arising from the fact that the mutant genes leading to higher branching may be recessive and that in this case corresponding mutations of both the duplicated genes in higher ploidy strains are necessary before a hereditary characteristic can be passed on by asexual reproduction. *Fungi imperfecti* differ from other fungi in that they do not normally pass through a sexual stage. Thus, it can be predicted that higher ploidy strains will generally show greater stability in inherited characteristics than haploid strains providing that they are cultured under conditions such that reversion or partial reversion of the haploid form is negligable.

By "higher ploidy" is meant higher ploidy than haploid including anenploid.

This invention comprises a human food product which comprises higher ploidy strain of a member of the *Fungi imperfecti* of which each parent has a genetic constraint on its ability to grow which is not shared by the other parent. The invention also comprises a higher ploidy strain of Fusarium. Preferably one parent is auxotrophic for two compounds selected from histidiine, arginine, leucine and adenine and the other is auxotrophic for the other two of the said compounds. Suitable strains are deposited by Marlow Foods Limited, Station Road, Stokesley, Middlesbrough TS9 7AB, as IMI 369190, 369191 and 369192 with The International Mycological Institute, Bakeham Lane, Egham, Surrey TW20 9TY on Nov. 6, 1995.

The human foodstuffs derived from *Fungi imperfecti* preferably have a reduced nucleic acid content of preferably less than 2% by weight.

This invention comprises a higher ploidy strain of *Fungi imperfecti* which is dead and of which the nucleic acid content is less than 2% by weight. The fungus may be killed and its nucleic acid content simultaneously reduced to less than 2% by treatment with water at a temperature of at least 60° C.; the water may be its own growth medium.

The genetic constraint may be that each parent is auxotrophic for a different metabolite or that each produces a gene product which is necessary for growth which has a temperature or pH sensitively greater than that of the corresponding gene product of the other parent. By growing the higher ploidy strain in an appropriate environment (in the above cases one lacking the nutrients for which the parents are auxotrophic or one which has a temperature of pH at which neither parent can grow without a supply of the other's gene product) one can select against reversion to haploid strains, thus maintaining the increased morphological stability of the fungus.

The invention also comprises human food which comprises a higher ploidy strain of *Fungi imperfecti* in which the fungus has been treated to remove nucleic acids and/or to modify its texture, taste or mouth feel.

The higher ploidy strains may be produced as follows. A corresponding haploid strain is cultured and subjected to mutagenesis, for example by ultra violet radiation until auxotrophic strains are produced which have lost the ability to make specific metabolites. The culture may be plated out for example onto agar plates and supplied with a complete medium which enables auxotrophs as well as unmutated organisms to grow. By replicate plating onto a minimal medium the unmutated strains are identified and the auxotrophs selected from the complete medium plate and their nutrient requirements identified. Two auxotrophs, for example, requiring different amino acids as nutrients may then be selected and used to produce a higher ploidy strain as subsequently described, or they may be cultured separately and the process repeated (except that in this case the minimal nutrient will contain the appropriate amino acid(s) required by each auxotroph). By this means two double auxotrophs may be derived each of which preferably requires two amino acids both of which differ from those required by the other. If desired triple or higher order auxotrophs may be prepared by corresponding means; they should preferably be auxotrophic for a group of metabolites which have no common member.

The invention comprises a process of preparing a higher ploidy strain of a member of the fungi imperfecti, for example Fusarium which comprises culturing two auxotrophs which require different auxotrophic nutrients together in a medium containing the nutrients necessary for both to grow (the joint culture stage) and then culturing organisms derived from such culture in a medium lacking the auxotrophic components (minimal medium) (the minimal medium culture stage) and recovering a higher ploidy strain from the minimal medium culture stage.

In the joint culture stage it is necessary to induce sporulation. This may be carried out by known means, suitably by subjecting the organisms to a nutritional challenge, for example by supplying only a complex carbon source as the main nutrient.

We have found that when transferred to a minimal nutrient medium, i.e. one lacking the auxotrophic components the higher ploidy strains derived from both auxotrophs multiply relative to the haploid strains and those higher ploidy strains derived from the same auxotroph, and that this effect may be increased by subjecting the organisms to a mutagen, which is suitably radiation, for example ultra violet light, at an intensity sufficient to kill a high proportion of haploid strains present.

It is preferred that higher ploidy strains should then be selected, for example by plate culture, using increased resistance to mutagenesis, for example by ultra violet light as a criterion for selection. If necessary selected organisms may be again cultured in a minimal medium, if desired under mutagenesis, for example by ultra violet light and surviving higher ploidy strains again selected.

From the higher ploidy strains produced as above a further selection may be made for other characteristics such as growth rate.

EXAMPLE

1.1 Parental Haploids

Fusarium strain A3/5 (CMI 145425, ATCC 20334) is the haploid wild type. Strains UMDA4-C and UMDA6-N were recovered from a suspension of A3/5 spores which had been subjected to ultra-violet irradiation using conventional mutation techniques. Both are double autotrophs. UMDA4-C has nutritional requirements for histidine and arginine and is more resistant to chlorate than A3/5. UMDA6-N requires leucine and adenine and is more resistant to nitrogen mustard than A3/5.

1.2 Culture Maintenance and Preparation of Seed Cultures

The organisms were maintained as hyphal fragments in 50% (v/v) glycerol and stored in vials (2 ml) held at $-196°$ C. Seed cultures were prepared by transferring aliquots from one of these vials to one liter Ehrlenmeyer flasks containing 50 ml or 200 ml of RHM growth medium (see below). Cultures were developed by incubating at 28° C. for up to 72 h.

1.3 Growth Media
1.3.1 RHM Medium

Amounts per liter: d-glucose, 10 g; $K_2SO_4$, 0.3 g; NH4Cl, 4.4 g; $MgSO_4.7H_2O$, 0.25 g; $KH_2PO_4$, 20.0 g; trace elements solution$^A$, 5.0 ml; biotin, 30 μg.

$^A$One liter of trace elements solution contained: $CaCl_2.2H_2O$, 2.0 g; $FeCl_3. 6H_2O$, 2.0 g; Citric acid, 1.5 g; $ZnCl_2$, 1.0 g; $MnCl_2.4H_2O$, 1.0 g; $CuCl_2.2H_2O$, 0.2 g; $CoCl_2.2H_2O$, 0.2 g; $NaMoO_4.2H_2O$, 0.2 g.

Minimal salts (excluding glucose and biotin) were combined and the pH adjusted to 6.0 using 20% (w/v) NaOH. The resulting solution was then dispensed as required into flasks. Glucose was prepared separately as a stock solution containing 500 g $l^{-1}$ d-glucose. Both were sterilised by autoclaving at 121° C. for 20 min. After cooling each flask was supplemented with glucose as required. Biotin was also added from a separate filter sterilised stock solution containing 30 mg $l^{-1}$ biotin.

1.3.2 YPG Medium

Amounts per liter: yeast extract, 3 g; mycological peptone, 5 g; D-glucose, 10 g. The yeast extract and peptone were combined to form a basal solution which was sterilised by autoclaving at 121° C. for 20 min. Glucose was then added from a separate stock solution containing 500 g $l^{-1}$ D-glucose prepared as described in section 1.3.1.

1.3.3 CMC Medium

Amounts per liter: Carboxymethylcellulose (CMC), 15 g; $NH_4NO_3$, 1.0 g; $KH_2PO_4$, 1.0 g; $MgSO_4.7H_2O$, 0.5 g. The components were dissolved and the pH adjusted to 6.0 using 20% NaOH before sterilising by autoclaving at 121° C. for 20 min.

1.3.4 Fermenter Medium

This was made from three separate stock solutions each prepared in volumes of 10 l and sterilised by autoclaving at 121° C. for 30 min.

a) Minimal Salts Concentrate

Amounts per 10 l; $K_2SO_4$, 40 g; $MgSO_4. 7H_2O$, 18 g; $(CH_3COO)_2Ca$, 4 g; $H_3PO_4$ (85% v/v), 23 ml; trace elements solution, 10 ml. One liter of trace elements solution contained: $MnSO_4. 4H_2O$, 40 g; $ZnSO_4. 7H_2O$, 50 g; $CuSO_4. 5H_2O$, 5 g; Biotin, 50 mg; $cH_2SO_4$, 5 ml.

b) Glucose

Stock solutions containing 66 g $l^{-1}$ D-glucose were prepared by dissolving 730 g of glucose monohydrate with water to a total volume of 10 l.

c) Iron

Amounts per 10 l: $FeSO_4. 7H_2O$, 5 g; $cH_2SO_4$, 5 ml.

Vessels containing the minimal salts concentrate and glucose solution were joined together after autoclaving and the contents mixed to form the principal nutrient stream. The iron solution, containing approximately 100 mg $l^{-1}$ $Fe^{2+}$, was supplied independently.

1.3.5 Supplemented Media

Arginine, histidine, leucine and adenine were added as required to minimal media at a concentration of 500 mg $l^{-1}$.

1.3.6 Solid Media

Where solid media were required 15 g $l^{-1}$ agar was added prior to autoclaving. The molten agar was allowed to cool to 55° C. after sterlisation and then swirled thoroughly to mix before dispensing aliquots of approximately 20 ml into 9 cm Petri dishes.

1.4 Formation and Isolation of Heterokaryons

Liquid cultures of the double auxotrophs were prepared as described in section 1.2 using RHM medium (50 ml) supplemented with arginine and histidine or adenine and leucine as appropriate. Sporulation was then induced by subculturing both strains in CMC medium to which arginine, histidine, adenine and leucine were added and the flasks incubated at 28° C. for a further 24 h. The resulting macrocondiial suspensions were mixed in a 1:1 ratio and 40 μl aliquots transferred to individual chambers of 10×96 well sterile microtest plates to which 160 μl of sterile YPG medium had been added. After mixing the plates were incubated at 28° C. for 48–72 h. In some cases this included a period of exposure to either camphor or ultra-violet irradiation: Camphor Plates were incubated for 4 hours at 28° C. in an atmosphere of camphor by placing them in a sealed container with a few crystals of d-camphor sprinkled in the bottom. After treatment the plates were removed and incubated in air for a further 44 h at 28° C. Ultra-violet Plates were incubated conventionally at 28° C. for 48 h then removed and exposed to ultra-violet light at 20 $\mu W.cm^{-2}$ for 210 sec. After exposure the plates were returned to 28° C. and incubated for a further 24 h.

Aliquots (10 $\mu$l) were removed from each well at the end of the incubation periods and mixed with 190 $\mu$l of RHM medium in a second set of microtest plates. These were then incubated at 28° C. for 7 days to highlight prototrophic growth.

1.5 Screening and Isolation of Putative Polyploids

New microtest plates containing wells primed with 190 $\mu$l of RHM medium were inoculated with 10 $\mu$l aliquots from cultures which had shown evidence of prototrophic growth. The plates were then incubated for 5 days at $28°$ C. and the cycle repeated twice to highlight strains which were able to grow consistently in minimal medium. Volumes were then scaled up by transferring 100 $\mu$l of the selected cultures to universal bottles containing 5 ml of RHM medium. These were incubated with agitation for up to 4 days at 28° C.

Strains recovered from the above screening protocol were subcultured in liquid once more by transferring 2 ml of culture from the universal bottles to flasks containing 50 ml of RHM and CMC growth medium. Both were incubated with agitation at 28° C. for 4 days. The contents were then harvested and used to prepare stock cultures for long term storage.

1.6 Analysis of Strains Using Dose-response to Ultra-violet Irradiation

Seed cultures of the desired strains were grown in flasks containing 50 $\mu$l RHM medium with supplements added as required for the double auxotrophs. Each flask was incubated with agitation at 28° C. for up to 48 h then subcultured by transferring 10 ml to a second flask containing 50 ml CMC medium. This was incubated under the same conditions for 16–20 h to promote sporulation. Vegetative mycelium was then removed by filtering through 2 layers of sterile lens tissue into a sterile container before transferring 20 ml of the spore suspension to a 9 cm Petri dish. The suspension was stirred continually using a magnetic stirrer unit.

Each plate was irradiated with ultra-violet light for up to 10 min. using an overhead lamp and a power rating of 20 $\mu W.cm^{-2}$. Viability was measured throughout the period of exposure by diluting 0.5 ml samples serially in Ringers' solution and spreading 0.2 ml volumes of each dilution onto plates containing agar solidified RHM medium (supplemented as appropriate). These were incubated at 28° C. and the number of colonies present at 48 h used to construct time series plots of the mean viable number. From these it was possible to quantify the exposure times associated with given levels of kill for each of the strains.

1.7 Continuous-flow Cultures

Cultures were grown in a Braun (B.Braun Biotech, Aylesbury, Bucks) Biostat ER3 fermenter with a working volume of 2.8 liters. The imposed set points were : temperature 28° C.; pH 6.0 (maintained by autotitration of 7 M $NH_4OH$); agitation 1000 rpm; air flow rate 2.21 l $min^{-1}$. Foaming was suppressed by the timed addition of polypropylene glycol antifoam oil at a rate of 0.1–0.2 ml $h^{-1}$.

The fermenter vessel was filled with minimal salts+glucose solution then supplemented with iron sulphate to give a final $Fe^{2+}$ concentration of 1 mg $l^{-1}$ in the growth medium. Control set points were established and the inoculum culture introduced. Growth was monitored by on-line analysis of the off-gas composition by mass spectrometry which was used to determine rates of carbon dioxide evolution (CER). Continuous-flow culture was established by switching on pumps delivering antifoam, iron and minimal salts+glucose when the CER had reached 35 m mol $l^{-1}$ $h^{-1}$. Iron was added at a fixed rate equivalent to an $Fe^{2+}$ concentration of 0.8–1.0 mg $l^-$ in the inflowing growth medium.

A feedback loop incorporating CER as the central controlled variable was used to regulate the flow rate of the minimal salts+glucose stream during continuous-flow. Signals received from the mass spectrometer were processed by software which was programmed to generate one of two output voltages in response to changes above or below the CER set point. The output voltage controlled the rotational speed of a peristaltic pump delivering the minimal salts+glucose stream and therefore the dilution rate since this stream alone accounted for over 95% of the total liquid flow passing into the fermenter. In practice the two output voltages corresponded to dilution rates of between 0.15 and 0.25 $h^{-1}$. These were designed to either further concentrate or dilute the biomass respectively. Regulated switching between the two limits was carried out under supervision by the software and the equilibrium maintained at a value which corresponded to the organism's maximum growth rate. This method of operation enabled excess levels of glucose to be maintained in the culture broth whilst operating at the maximum permissible dilution rate.

Monitoring of Colonial Morphology

Samples of fresh culture were removed daily from the fermenter and diluted serially in sterile Ringers solution. Aliquots (0.1 ml) of the appropriate dilutions were spread onto the surface of 10 agar plates containing solidified RHM medium. These were incubated at 28° C. for up to 72 h. and the proportion of colonial variants determined as described by (Wiebe et al., 1991).

2 RESULTS

2.1 Selective Recovery of Prototrophs

A total of 34,650 individual matings were carried out; 11,520 had no special treatment; 11,520 were exposed to camphor and 11,520 were irradiated using ultra-violet light. Table 1 gives the number of prototrophs obtained with each method after three (penultimate) and four (final) selective subcultures in RHM minimal medium.

TABLE 1

| | Selective recovery of prototrophs using three variations of the microtest method | | | |
|---|---|---|---|---|
| Mating Treatment | Number Screened | Third subculture | Fourth subculture | Recovery frequency |
| None | 11,520 | 0 | 0 | 0 |
| Ultra violet | 11,520 | 113 | 1 | $8.7 \times 10^{-5}$ |
| D-Camphor | 11,520 | 46 | 12 | $1.0 \times 10^{-3}$ |

Prototrophs were not recovered from the conventional crosses, ie those which did not expose cultures to either camphor or ultra-violet light, indicating that the natural recovery frequency for prototrophic growth is less than $8.7 \times 10^{-5}$. Treatment with camphor was clearly the most successful method yielding a total of 12 strains and increasing recovery frequency by at least two orders of magnitude ie $1 \times 10^{-3}$. These strains were assigned the strain codes D2 and D11–D21.

The screen incorporating ultra-violet irradiation produced only one culture of interest (code 11-1/M1) which initially contained two variants with different colonial morphologies. These were subsequently called "large" or "small" because of their relative differences in diameter. The larger of the two types was also more vigorous with an apparently greater hyphal density than the smaller one. Dose-response tests (1.6) showed that the large type was more resistant to ultra-violet irradiation suggesting an intrinsically lower mutation frequency. On this basis it was decided to concentrate primarily on this type and the smaller type was therefore discounted. A total of 9 individual large colonies which had grown on dilution plates prepared during the dose-response test were recovered as sub-clones and assigned the strain codes D1 and D3–D10.

The geneaology of these and the 12 cultures which had been treated with camphor is summarised in FIG. 1.

2.2 Analysis of Strains Using Dose-response to Ultra-violet Irradiation

Exposure (or kill) times corresponding to a 90, 99 and 99.9% reduction in viable count were used to quantify the dose-response for each strain (Table 2).

TABLE 2

Comparison of ultra-violet exposure times giving 90, 99 and 99.9% kill in spore suspensions of parental haploids and putative polyploids of *F. graminearum*

| Strain codes Putative Higher ploids | Initial viable count | Exposure time giving 90% kill | Exposure time giving 99% kill | Exposure time giving to 99.9% kill |
|---|---|---|---|---|
| D1 | $2.5 \times 10^6$ ml$^{-1}$ | 5.5 | 13* | >10 |
| D2 | $4 \times 10^6$ ml$^{-1}$ | 5.9 | >10 | >10 |
| D3 | $1.8 \times 10^6$ ml$^{-1}$ | 4.4 | 8.3 | >10 |
| D4 | $9.5 \times 10^5$ ml$^{-1}$ | 4.8 | 9.1 | >10 |
| D5 | $1.7 \times 10^6$ ml$^{-1}$ | 3.2 | 4.4 | 5.9 |
| D6 | $1.5 \times 10^6$ ml$^{-1}$ | 5.4 | 8.5 | >10 |
| D7 | $1.3 \times 10^6$ ml$^{-1}$ | 4.2 | 7.7 | >10 |
| D8 | $4 \times 10^6$ ml$^{-1}$ | 4.5 | 6.6 | >10 |
| D9 | $6.5 \times 10^6$ ml$^{-1}$ | 4.9 | 7.8 | >10 |
| D10 | $3 \times 10^6$ ml$^{-1}$ | 4.1 | 8.5 | >10 |
| D11 | $3.5 \times 10^5$ ml$^{-1}$ | 5.2 | >10 | >10 |
| D12 | $1.4 \times 10^6$ ml$^{-1}$ | 5.7 | 8.7 | >10 |
| D13 | $5.5 \times 10^5$ ml$^{-1}$ | 5.2 | 9.5 | >10 |
| D14 | $3.5 \times 10^6$ ml$^{-1}$ | 3.5 | 7.2 | >10 |
| D15 | $2.6 \times 10^6$ ml$^{-1}$ | 5.3 | >10 | >10 |
| D16 | $9 \times 10^5$ ml$^{-1}$ | 5.9 | >10 | >10 |
| D17 | $2 \times 10^6$ ml$^{-1}$ | 6.8 | >10 | >10 |
| D18 | $5 \times 10^5$ ml$^{-1}$ | 4.9 | 8.4 | >10 |
| D19 | $1.1 \times 10^6$ ml$^{-1}$ | 1.9 | 3.6 | >10 |
| D20 | $1.6 \times 10^5$ ml$^{-1}$ | 10.5* | >10 | >10 |
| D21 | $1.8 \times 10^6$ ml$^{-1}$ | 2.8 | 4.9 | 9.9 |
| Parent Haploids | | | | |
| A3/5 | $2.3 \times 10^6$ ml$^{-1}$ | 4.4 | 5.7 | 7.4 |
| UMDA4-C | $1.5 \times 10^6$ ml$^{-1}$ | 7.4 | >10 | >10 |
| UMDA6-N | $3.9 \times 10^6$ ml$^{-1}$ | 5.7 | 9.2 | >10 |

All times in minutes
*Obtained by extrapolation

Organisms D1, D2 and D21 have been deposited under the provisions of the Budapest Treaty under deposit numbers IMI 369192, IMI 369191 and IMI 369190 with the International Mycological Institute, Bakeham Lane, Egham, Surrey TW20 9TY, United Kingdom on Oct. 19, 1995.

For A3/5 the respective kill times were 4.4, 5.7 and 7.4 minutes. In the case of the double auxotrophs it was evident that longer exposure periods were needed to establish a full complement of comparative data because values representing the 99.9% kills (and 99% for UMDA4-C) did not fall within the 10 minutes exposure period.

In general the values representing 90 and 99% kills for presumptive higher ploids from the ultra-violet matings were of the same order of magnitude as those recorded for the parental haploids. Most of the group reflected 90% kill times that were within 0.5 min of that obtained for A3/5 i.e. 3.9–4.9 minutes although there was evidence that two of the strains (D1 and D5) were different from the rest. Values for D1 were higher than those of other isolates in the group whilst the values for D5 were consistently lower. The profiles indicated that D1 was similar to the double auxotrophs i.e. more resistant than A3/5 and that D5 was marginally less resistant than A3/5.

By contrast half of the isolates recovered from the camphor matings required exposure periods of more than 10 min. to force a 99% kill. A large proportion were grouped within the 4.9–6.8 min range although there were four notable exceptions. Strains D14, D19 and D21 appeared to be more susceptible whilst D20 was clearly the most resistant not only of the camphor group but of all the prototrophs isolated during the course of the programme.

2.4 Appearance of Colonial Variants in Continuous-flow Cultures of D1 and D2

Variants with a restricted colonial phenotype are normally detected in continuous-flow cultures of A3/5 after periods of 107+/−14 generations ie 448+/−60 h. However, variants with a restricted colonial phenotype were not detected in fermentations conducted with D1 and D2 until 540 and 594 generations (1,957 and 2,028 h) respectively. (Table 3). The increased stability therefore approximates to at least a four fold increase in the productive run length of commercial QUORN® fermentations.

TABLE 3

First appearance of restricted colonial mutants in continuous-flow cultures of Fusarium A3/5, D1 and D2

| Strain Code | Average dilution rate in continuous flow (h$^{-1}$) | Time after onset of continuous flow (h) | Generations after onset of continuous flow |
|---|---|---|---|
| A3/5 | 0.17 | 448 +/− 60 | 107 +/− 14 |
| D1 | 0.19 | 1,957 | 540 |
| D2 | 0.2 | 2,028 | 594 |

TABLE 4

Occurence of the Parasexual Cycle in fungi

| Class | Species | Comment | Reference |
|---|---|---|---|
| Ascomycotina | Eurotium (Aspergillus) nidulans | Model fungus | Roper (1952) |
| Basidiomycotina | Corprinus cinereus | Corprophilous fungus | Casselton (1965) |
| | Ustilago maydis | Smut pathogen of maize | Holliday (1961) |
| Deuteromycotina | Acremonium chrysogenum | Used to produce cephalosporin C. | Nuesch et al (1973) |
| | Aspergillus niger | Used to produce citric acid | Pontecorvo et ai (1953) |
| | Aspergillus sojae | Used in koji fermentations | Ishitani et ai (1956) |
| | Penicillium chrysogenum | Used to produce penicillin | Pontecorvo & Sermontii (1954) |
| | Penicillium expansum | Pathogen of apples | Barron (1962) |
| | Verticillium albo-atrum | Pathogen of hops | Hastie (1962) |
| | Verticillium dahliae | Wide-ranging crop pathogen | Hastie (1962) |
| | Verticillium lecanii | Pathogen of insects | Jackson & Heal (1983) |
| | Fusarium oxysporum | Pathogen of peas | Buxton (1956) |

REFERENCES

BALL, C., LAWRENCE, A. J., BUTLER, J. M. & MORRISON, K. B. (1978). *European Journal of Applied Microbiology and Biotechnology* 5, 95–102.

BARRON, G. L. (1962). The parasexual cycle and linkage relationships in the storage rot fungus *Penicillium expansum*. *Canadian Journal of Botany* 40, 1603–1613.

BOOTH, C. (1984). The Fusarium problem: historical, economic and taxonomic aspects. In: *The Applied Mycology of Fusarium* (ed. M. O. Moss & J. E.Smith), pp. 1–14. London: British Mycological Society.

BU'LOCK, J. D., MOONEY, J. P. & WRIGHT, C. E. (1986). Regulation of mycotoxin production by *Fusarium graminearum*: complementation effects between two mutant types. *Biotechnology Letters* 8 (5), 323–326.

BUXTON, E. W. (1956). Heterokaryosis and parasexual recombination in pathogenic strains of *Fusarium oxysporum*. *Journal of General Microbiology* 15, 133–139.

CALAM, C. T., DAGLISH, L. B. & McCANN, E. P. (1976). In: *Proceedings of the Second International Symposium on the Genetics of Industrial Microorganisms*. (ed. K. D. MacDonald) pp. 273–287. London: Academic Press.

CASSELTON, L. A. (1965). The production and behaviour of diploids of *Corprinus lagopus*. *Genetical Research* 6, 190–208

CATEN, C. E. (1981). Parasexual processes in fungi. In: *The Fungal Nucleus* (eds. K. Gull and S. T. Oliver) pp. 191–214. Cambridge: Cambridge University Press.

CHANG, L. T., TERESAKA, D. T. & ELANDER, R. P. (1982). *Developments in Industrial Microbiology* 23, 21–29.

CRUEGER, A. (1982). In: *Fourth International Symposium on the Genetics of Industrial Microorganisms*. Abstract 0-V1-1.

DAS, A. & ROY, P. (1978). Improved production of citric acid by a diploid strain of *Aspergillus niger*. *Canadian Journal of Microbiology* 24, 622–625.

ELANDER, R. P., ESPENSHADE, M. A., PATHAK, S. G. & PAN, C. H. (1973). In: *Proceedings of the First International Symposium on the Genetics of Industrial Micrrganisms* (eds. Z. Vanek, Z. Holstalek & J. Cudlin) pp. 239–253. Amsterdam: Elsevier Publishing Co.

HAMLYN, P. F. & BALL, C. In: *Proceedings of the Third International Symposium on the Genetics of Industrial Microrganisms* (eds. O. K. Sebek & A. I. Laskin) pp. 185–191. Washington D.C.: American Society for Microbiology.

HASTIE, A. C. (1962). Genetic recombination in the hop-wilt fungus *Verticillium albo-atrum*. *Journal of General Icrobiology* 27, 373–382.

HASTIE, A. C. (1970). The genetics of asexual phytopathogenic fungi with special reference to Verticillium. In: *Root Disesases and Soil-borne Pathogens* (eds. T. A. Tousson, R. V. Bega & P. E. Nelson) pp. 55–62. Berkeley: University of California Press HOLLIDAY, R. (1961). Induced mitotic crossing-over in *Ustilago maydis*. *Genetical Research* 2, 231–248.

ISHITANI, C., IKEDA, Y. & SAKAGUCHI, K. (1956). Hereditary variation and genetic recombination in Koji-molds (*Aspergillus oryzae* and *Aspergillus sojae*). VI. Genetic recombination in heterozygous diploids. *Journal of General and Applied Microbiology* (Tokyo) 2, 401–430.

JACKSON, C. W. & HEALE, J. B. (1983). Protoplast fusion to overcome vegetative incompatibility in *Verticillium lecanii* parasexual genetics. In: *Protoplasts 1983. Poster Proceedings, 6th international Protoplast symposium*, Basel, Aug. 12–16, 1983, pp 318–319. Basel: Birkhauser Verlag.

JOHNSON, J. R. (1975). Strain improvement and strain stability in filamentous fungi. In: *The Filamentous Fungi Vol. 1*. (eds. J. E. Smith & D. R. Berry) pp. 59–78. London: Edward Arnold.

NUESCH, J., TREICHLER, H. J. & LIERSCH, M. (1973). The biosynthesis of cephalosporin C. In: *Genetics of Industrial Microorganisms, Actinomycetes and Fungi* (eds. Z. Vanek, Z. Hostalek & J. Cudlin) pp. 309–334. Prague: Academia.

PAQUIN, C. & ADAMS, J. (1983). Frequency of fixation of adaptive mutations is higher in evolving diploid than haploid yeast poulations. *Nature* 302, 495–500.

PEBERDY, J. F. (1988). Genetic manipulation. In: *Physiology of Industrial Fungi* (ed. J. F. Peberdy), pp. 187–218. Oxford: Blackwell Scientific Publications.

PONTECORVO, G., ROPER, J. A. & FORBES, E. (1953). Genetic recombination without sexual reproduction in *Aspergillus niger*. *Journal of General Microbiology* 8, 198–210.

PONTECORVO, G. & SERMONTI, G. (1954). Recombination without sexual reproduction in *Penicillium chrysogenum*. *Nature* 172, 126–127.

REHM, H. J. & REED, G. (1981). Genetic systems in industrial micro-organisms. In: *Biotechnology, Vol. I Microbial Fundamentals* (eds. H. F. Ebel and C. Schultz) pp. 246–251. Basel: Verlag Chemie.

ROPER, J. A. (1952). Production of heterozygous diploids in filamentous fungi. *Experientia* 8 (1), 14–15.

ROPER, J. A. (1966). The parasexual cycle. In: *The Fungi, Volume II, The Fungal Organism* (eds. G. C. Ainsworth & A. S. Sussman) pp. 589–617. New York: Academic Press.

ROWLANDS, R. T. (1984). Industrial strain improvement: rational screens and genetic recombination techniques. *Enzyme & Microbial Technology* 6, 290–300.

STERN, C. (1936). Somatic crossing-over and segregation in Drosophila melanogaster. *Genetics* 21, 625–630.

TAKEDA CHEMICAL COMPANY (1977). [Production of cephalosporin C]. *British Patent Number* 1 488 822.

WIEBE, M. G., TRINCI, A. P. J., CUNLIFFE, B, ROBSON, G. D & OLIVER, S. G., (1991) : Appearance of morphological (colonial) mutants in glucose-limited continuous-flow cultures of *Fusarium graminearum* A3/5. *Mycological Research* 95, 1284–1288.

WILLIAMS, M. A. J. & KIRK, P. M. (1988). Characteristics of industrial fungi. In: *Physiology of Industrial Fungi* (ed. J. F. Peberdy), pp. 1–17. Oxford: Blackwell Scientific Publications.

We claim:

1. A human food product which comprises a higher ploidy strain of a member of the genus Fusarium of which each parent has a genetic constraint on its ability to grow which is not shared by the other parent.

2. An edible higher ploidy strain of Fusarium of which each parent strain is auxotrophic for a different metabolite.

3. A strain according to claim 2 of which one parent is auxotrophic for two amino compounds selected from histidine, arginine, leucine and adenine and the other is auxotrophic for the other two of said compounds.

4. Fusarium strains IMI 369190, IMI 369191 and IMI 369192, and variants, mutants and derivatives thereof of higher ploidy which retain all of the identifying characteristics of the parent strains.

5. A higher ploidy strain of Fusarium which is dead and of which the nucleic acid content is less than 2% by weight.

6. A strain according to claim 5 of which each parent has a genetic constraint on its ability to grow which is not shared by the other parent.

7. A food product as claimed in claim 1, in which the strain is dead and its nucleic acid content is less than 2% by weight.

8. A process of preparing a strain of Fusarium as claimed in claim 5, which comprises killing a higher ploidy strain of Fusarium and simultaneously reducing its nucleic acid content to below 2% by weight by treatment with water at a temperature of at least 60° C.

9. A process as claimed in claim 1 in which the fungus is Fusarium A3/5.

10. A process of preparing a higher ploidy strain of edible Fusarium according to claim 2 which comprises culturing two auxotrophs thereof which require different auxotrophic nutrients together in a medium containing nutrients permitting both to grow (the joint culture stage) and then culturing organisms derived from such culture in a medium lacking the auxotrophic components (minimal medium) (the minimal medium culture stage) and recovering a higher ploidy strain from the minimal medium culture stage.

11. A process as claimed in claim 10 in which the auxotrophs are prepared by mutation and selection.

12. A process as claimed in claim 11 in which both auxotrophs are derived from the same strain.

13. A process as claimed in claim 10 in which the auxotrophs require different amino compounds as nutrients.

14. A process as claimed in claim 13 in which each auxotroph requires two amino compounds as nutrients neither of which is the same as is required by the other auxotroph.

15. A process as claimed in claim 10 in which fungi resulting from the joint culture stage are subjected to mutagenesis of sufficient severity to kill a substantial proportion of any haploid fungi present whilst permitting at least some higher ploidy fungi to survive whereby a greater proportion of higher ploidy than haploid fungi survive the mutagenesis.

16. A process as claimed in claim 10 in which fungi are subjected to mutagenesis during the minimal medium culture stage or after recovery therefrom, the mutagenesis being of sufficient severity to kill a substantial proportion of any haploid fungi present whilst permitting survival of at least some higher ploidy fungi whereby a greater proportion of higher ploidy than haploid fungi survive the mutagenesis.

17. A process as claimed in claim 15 or 16 in which the mutagenesis is carried out by radiation.

18. A process as claimed in claim 17 in which the radiation is ultra violet radiation.

19. A process of producing human food which comprises culturing a higher ploidy strain of Fusarium of which each parent has a genetic constraint on its ability to grow which is not shared by the other parent, which process is carried out under conditions such that reversion or partial reversion to the haploid form is minimized, and recovering the biomass produced, for use in human food.

20. Human food which comprises a higher ploidy strain of Fusarium in which the fungus has been treated by at least one of the methods of removing nucleic acids or modifying its texture, taste or mouth feel.

* * * * *